United States Patent
Valachovic et al.

(10) Patent No.: US 10,844,014 B2
(45) Date of Patent: Nov. 24, 2020

(54) INTERMEDIATES FOR THE PREPARATION OF REMIFENTANIL HYDROCHLORIDE

(71) Applicant: Hameln Pharma Plus GmbH, Hameln (DE)

(72) Inventors: Pavol Valachovic, Pezinok (SK); Janka Králová, Pezinok (SK); L'uboš Slížik, Senec (SK); Norbert Varga, Modra (SK)

(73) Assignee: HAMELN PHARMA GMBH, Hameln (DE)

( * ) Notice: Subject to any disclaimer, the term of this patent is extended or adjusted under 35 U.S.C. 154(b) by 0 days.

(21) Appl. No.: 16/664,464

(22) Filed: Oct. 25, 2019

(65) Prior Publication Data

US 2020/0131127 A1    Apr. 30, 2020

(30) Foreign Application Priority Data

Oct. 26, 2018    (EP) ..................................... 18202878

(51) Int. Cl.
*C07D 211/98*    (2006.01)

(52) U.S. Cl.
CPC ................. *C07D 211/98* (2013.01)

(58) Field of Classification Search
CPC ..................................................... C07D 211/98
USPC ......................................................... 546/244
See application file for complete search history.

(56) References Cited

U.S. PATENT DOCUMENTS

2010/0016601 A1*  1/2010  Cervello Pages .... C07D 211/58
                                                        546/244

OTHER PUBLICATIONS

Journigan, Journal of Medicinal Chemistry, 57(21), 8903-8927.*
European Search Opinion for EP 3 643 704 dated Jan. 4, 2019.
European Search Report for EP 3 643 704 dated Jan. 4, 2019.

* cited by examiner

*Primary Examiner* — Nizal S Chandrakumar
(74) *Attorney, Agent, or Firm* — Jenkins, Wilson, Taylor & Hunt, P.A.

(57) ABSTRACT

A new intermediate for synthesizing 1-substituted-4-[phenyl (propanoyl)amino]piperidine-4-carbonitrile derivatives is laid open. Specifically set out is a method for use of this intermediate in the preparation of remifentanil. The enclosed shorter process offers a greater yield of products with higher purity as compared to methods reported in the prior art.

12 Claims, No Drawings

INTERMEDIATES FOR THE PREPARATION OF REMIFENTANIL HYDROCHLORIDE

CROSS REFERENCE TO RELATED APPLICATION

This application is based on and claims priority to European Patent Application Serial No. EP 18202878.7, filed Oct. 26, 2018, the disclosure of which is incorporated by reference herein in its entirety.

FIELD OF INVENTION

The present invention relates to a process for the synthesis of fentanyl-type opioid analgesics. In particular, the present invention describes a new efficient synthetic route for the preparation of Remifentanil hydrochloride and precursors thereof.

BACKGROUND

Remifentanil hydrochloride (1) belongs to the 4-anilidopiperidine class of synthetic opioid analgesics.

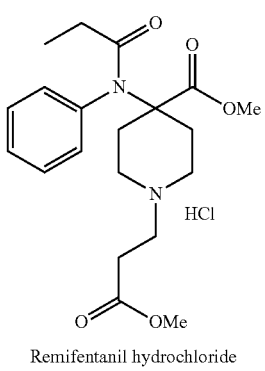

Remifentanil hydrochloride

It has a high degree of analgesic potency (ED50=0.0044 mg/kg) and due to its rapid onset and ultra-short duration of action (15 min.) it became a clinically useful addition to the fentanyl family of analgesics. Remifentanil in combination with a hypnotic drug can be administered in relative high doses due to its rapid elimination from the blood plasma. This means, that accumulation does not occur with Remifentanil and its context-sensitive half-life remains at 4 minutes after a 4-hour infusion. Remifentanil is metabolized by non-specific tissue and plasma esterases, which hydrolyses one of the ester groups. The formed Remifentanil acid has $\frac{1}{4600}$th the activity of the parent compound. The pharmacokinetics of Remifentanil also offers faster recovery after surgery.

The preparation of Remifentanil hydrochloride was disclosed in patent EP 0383579 A1 which describes the last two steps of the synthesis shown in scheme 1. Key intermediate 7 is prepared according to literature (P.G.H. Van Daele et al. Arzneim.-Forsch. Drug. Res. 1976, 26, 1521) in 5 steps starting form 1-benzyl-4-piperidone (2).

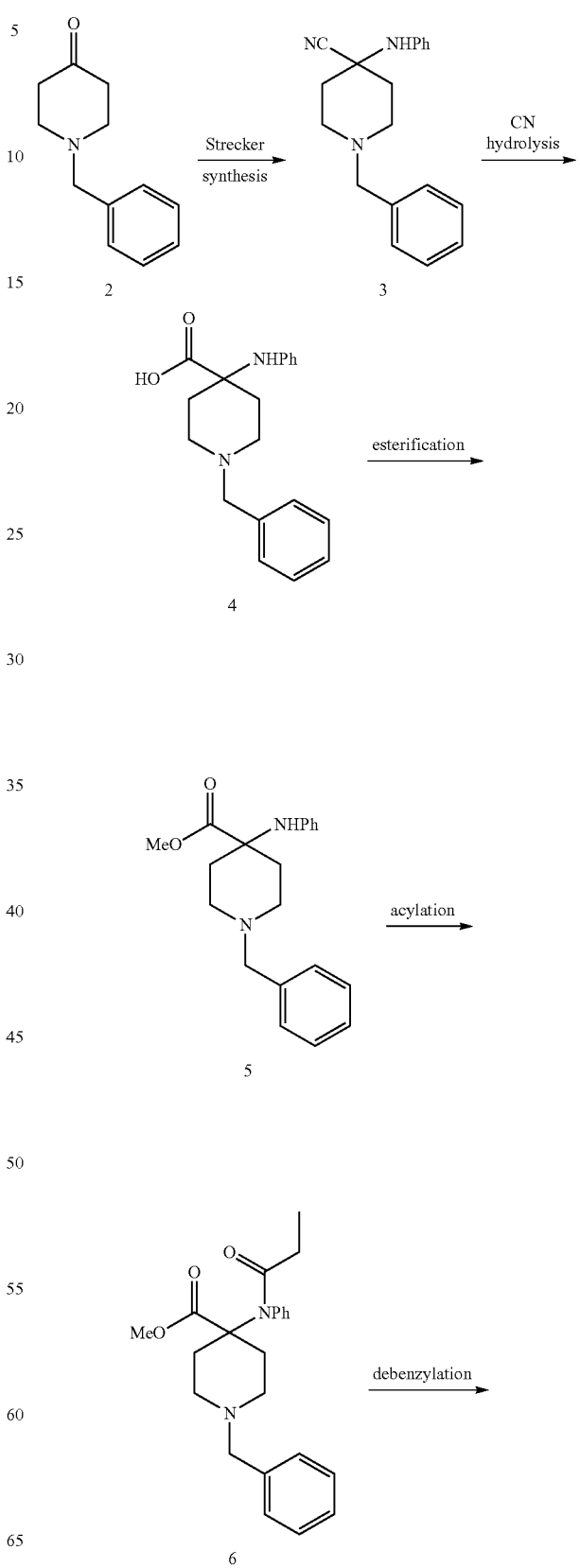

Scheme 1 Synthesis of Remifentanil hydrochloride according to patent EP 0383579 A1

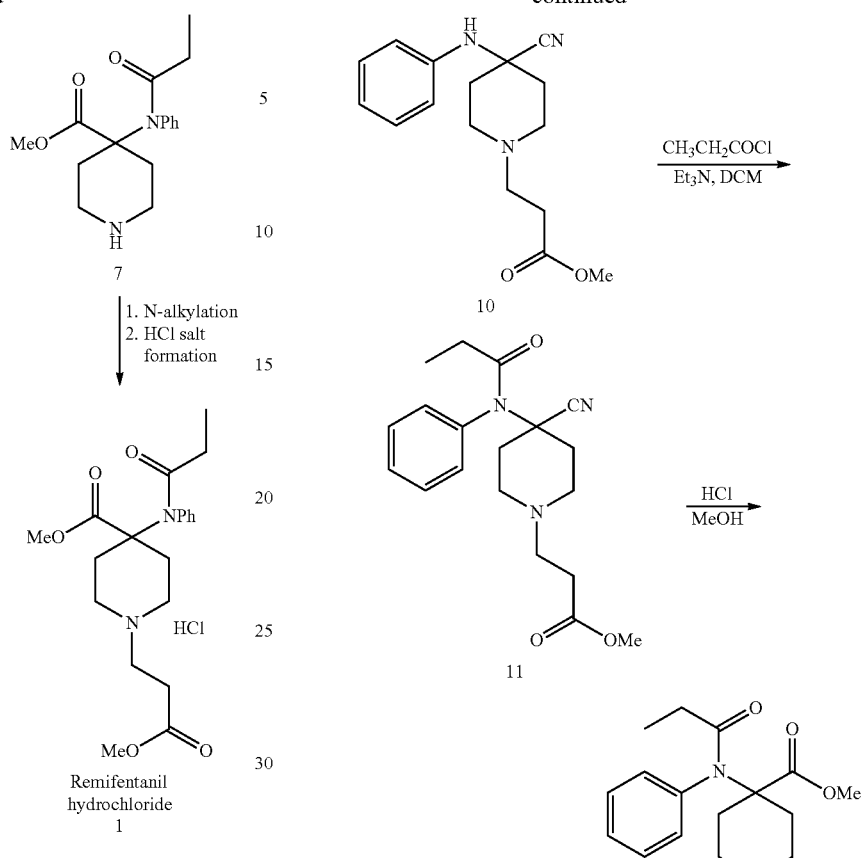

A 4 step synthesis is described in patent WO 2007144391 (Kern Pharma). Starting material 4-piperidone 8 is alkylated with methyl acrylate followed by the introduction of the aniline function and a nitrile group using Strecker synthesis. Acylation of the aniline nitrogen using propionyl chloride generates the precursor of Remifentanil hydrochloride (11). In the last step the nitrile group is converted into a methyl ester using methanol and HCl, thus affording the target molecule.

Hydrolyzation of nitrile groups in this synthesis are with low yields because of the ester group that is partly saponified under the conditions and side products are formed. The intermediates containing a methyl ester function are prone to fast hydrolysis.

Patent WO 2007061555 (Mallinckrodt Inc.) made a small alteration in the synthesis of Remifentanil HCl compared to patent WO 2007144391. The nitrile function in compound 10 is first hydrolyzed to an amide which is then converted to a methyl ester. In the final step the propionyl function is introduced. (Scheme 3)

Scheme 2 Preparation of Remifentanil hydrochloride according to patent WO 2007144391

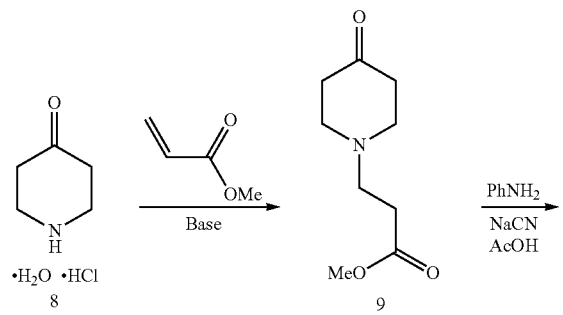

Scheme 3 Synthesis of Remifentanil hydrochloride claimed by patent WO 2007061555

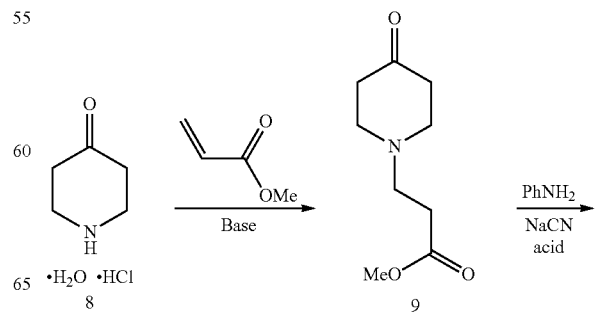

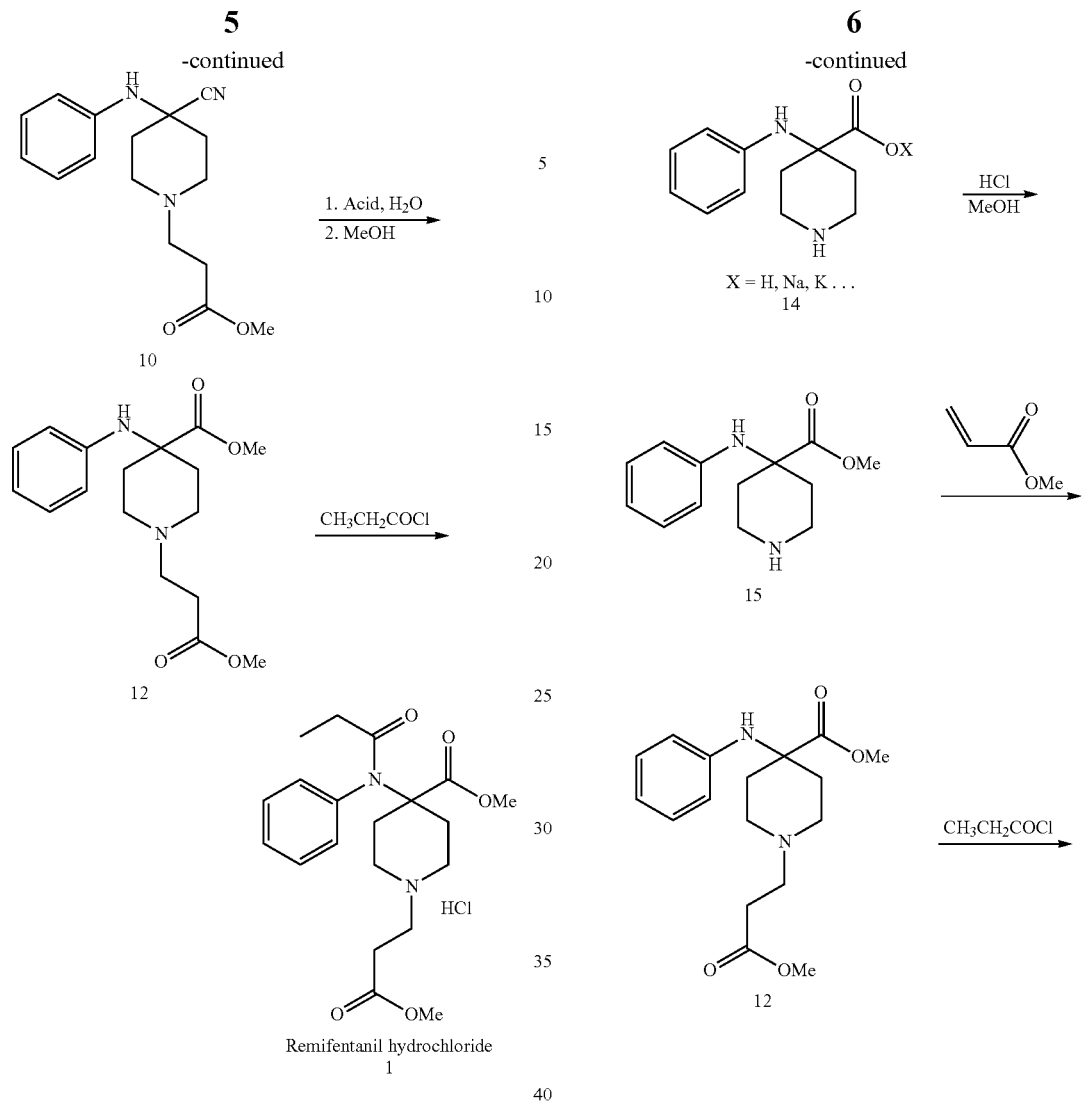

The synthesis of Remifentanil hydrochloride according to patent WO 2007087164 (Mallincrodt Inc.) starts with 1-(carbethoxy)-4-(phenylamino)-4-piperidine carboxamide, which is hydrolysed to carboxylic acid or carboxylate group simultaneously with deprotection of the piperidine nitrogen. In the following step the esterification of the carboxylic group with methanol is carried out. Alkylation of the piperidine amine with methylacrylate followed by the acylation of the secondary nitrogen with propionyl chloride generates Remifentanil hydrochloride (Scheme 4).

Scheme 4 Synthesis of Remifentanil hydrochloride claimed by patent WO 2007087164

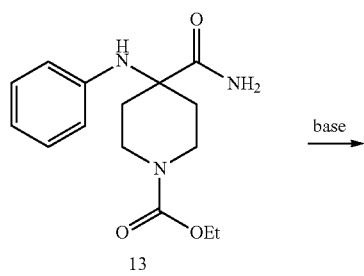

All the above mentioned synthetic routes used Michael addition to introduce the methyl propionyl function. In patent WO 2010053944 (Cambrex Charles City, Inc.) methyl 1-benzyl-4-(N-phenylpropionamido)piperidine-4-carboxylate is treated with 4-nitrophenyl sulfonic acid to create nosylate salt 17, which is then reacted under basic condition with methyl hydroxypropionate activated with a nosylate function (18). Acylation of the last intermediate with propionyl chloride gives the final API Remifentanil hydrochloride (Scheme 5).

Scheme 5 Synthesis of Remifentanil hydrochloride disclosed in patent WO 2010053944
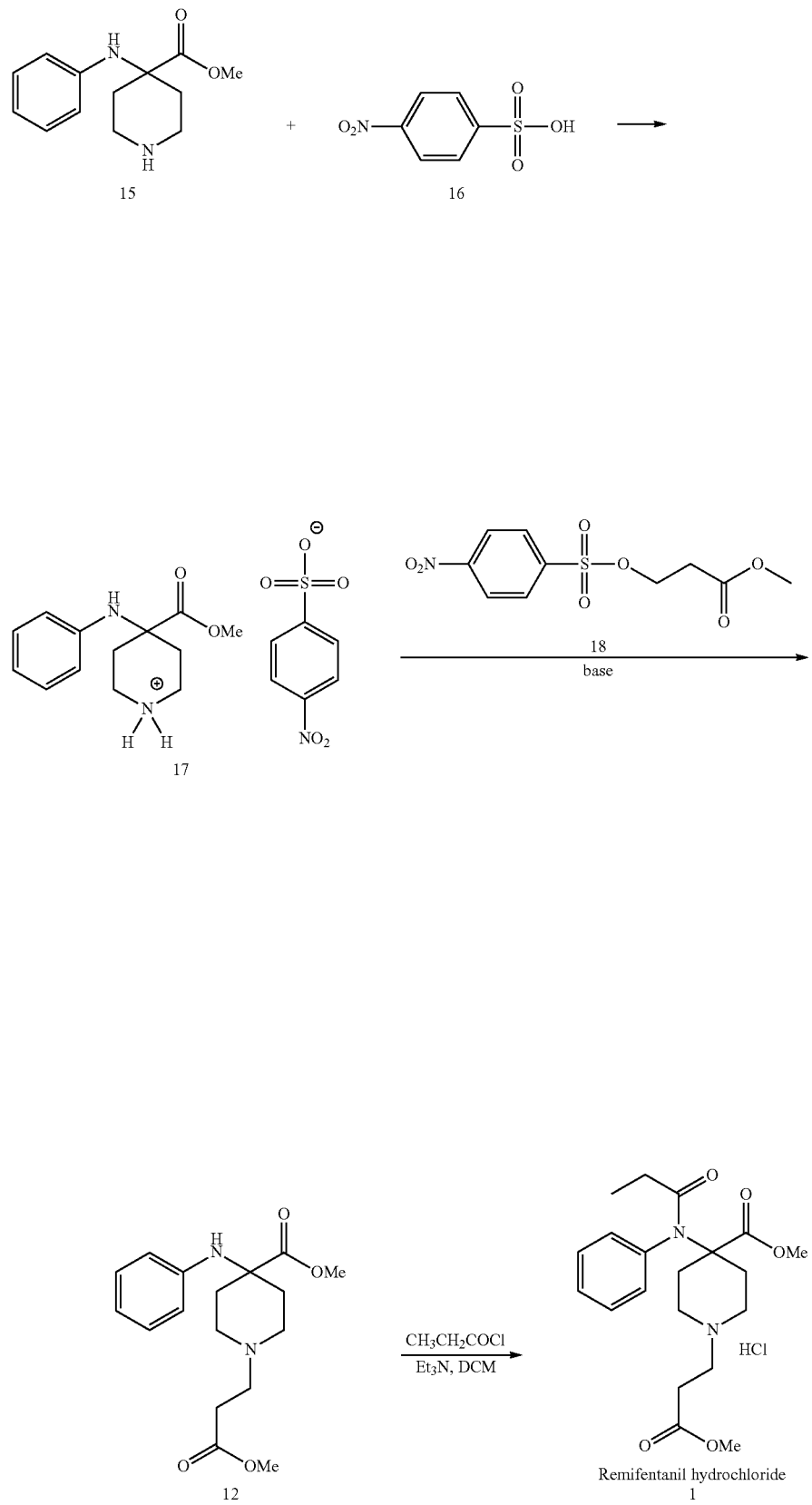

DETAILED DESCRIPTION

1. New Compounds

It has now been found two new intermediates that are useful in the synthesis of Remifentanil. Compound 20 and compound 21.

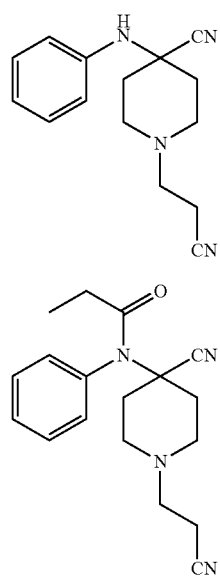

The use of intermediates containing two nitrile groups has many advantages compared to the synthesis as used so far. For example it gives the opportunity to exclude the Michael addition to the nitrogen side chain in the synthesis, thus deleting the use of alpha-beta unsaturated reagents such as acrylic acid ester in the reaction, which is suspect to show cytotoxic properties.

The use of intermediates containing two nitrile groups further gives the opportunity to deliberate the ester groups at two parts of the molecule within one single synthesis step, thus increasing the total yield of the total synthesis of Remifentanil.

2. Use of New Compound in the Synthesis of Remifentanil Compound 20 May be Used in Different Ways for the Synthesis of Remifentanil.

In one embodiment the compound is converted to the new compound 21, in another embodiment, compound 20 is transferred to a compound 12, that was already reported in patent applications as shown above.

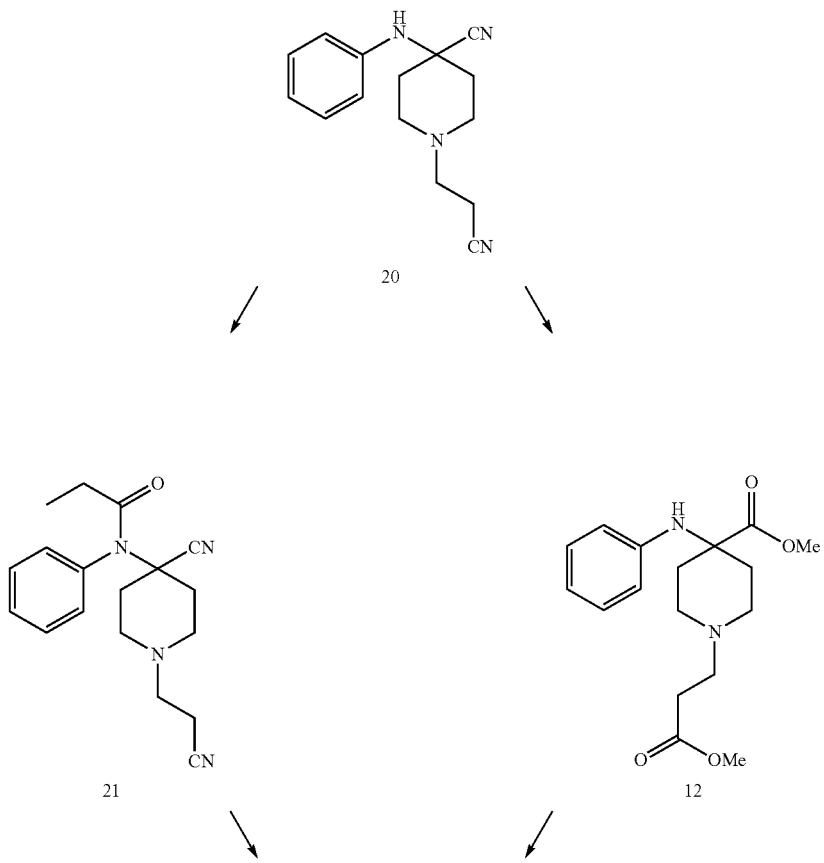

-continued

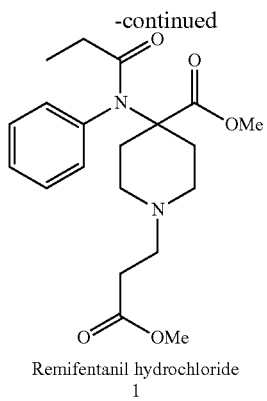

Remifentanil hydrochloride
1

3. Use of New Compound 20 in the Preparation of New Compound 21

In the first embodiment of the invention the new compound is acylated by an appropriate acylating agent to compound 21.

1-(2-cyanoethyl)-4-(phenylamino)piperidine-4-carbonitrile (20) reacts with an acylating agent in presence or without presence of a base to give 1-(2-cyanoethyl)-4-[phenyl(propanoyl)amino]piperidine-4-carbonitrile (21, Scheme 9)

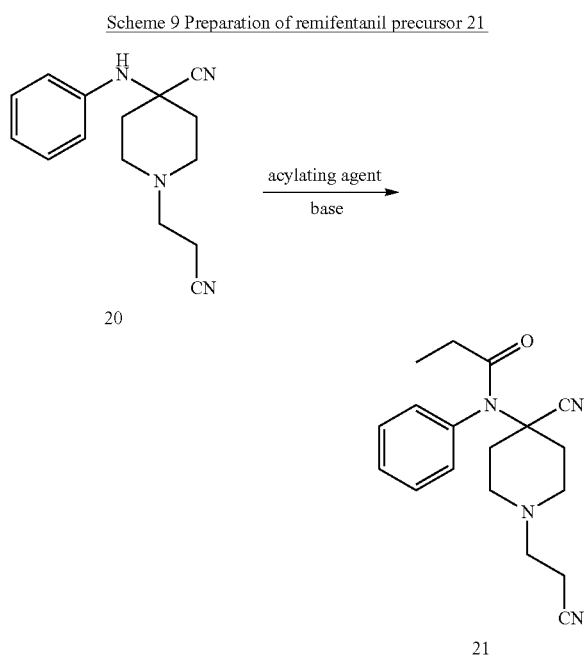

The reaction mixture comprises about 1 molar equivalent to about 10 molar equivalents of acylating agent. In one example the reaction mixture is charged with about 1 to 3 molar equivalent of acylating agent to 1 molar equivalent of 1-(2-cyanoethyl)-4-(phenylamino)piperidine-4-carbonitrile 20.

In one embodiment the reaction between compound 20 and acylating agent occurs in the presence of an acid scavenger (base), wherein the reaction mixture comprises about 1 molar equivalent to 3 molar equivalents of the acid scavenger.

The temperature of the reaction mixture during reaction ranges from about 0° C. to about 80° C. Preferably, the reaction temperature ranges from about 30° C. to about 50° C. The reaction mixture is allowed to react up to several days. In one example the reaction time is from about 10 hours to 30 hours.

In one embodiment the acylating agent is propionic anhydride. In another embodiment the acylating agent is propanoyl chloride. Both reagents show comparable yields in the reaction.

Examples of solvents used in the reaction mixture and crystallization include solvents that are inert to the reaction occurring in step 3. Examples of such solvents include, but are not limited to acetonitrile, acetone, dichloromethane, chloroform, N,N-dimethylacetamide, N,N-dimethylformamide, dimethylsulfoxide, tert-butyl methyl ether, diisopropyl ether, ethyl acetate, dichloroethane, benzene, toluene, xylene, 1,4-dioxane, tetrahydrofurane, 2-methyl tetrahydrofurane, methyl ethyl ketone and mixtures thereof. In one example the mixture contains dichloromethane. The compound 20 to solvent ration on wt. basis is about 1:10 to 1:50.

The acid scavenger can include metal hydrides, hydroxides, carbonates, bicarbonates, amines, and the like.

After the reaction is completed water and base are added to the reaction to adjust the pH to above 7. Solvent extraction is done with an organic solvent. The solvent is removed under reduced pressure to obtain the crude product. The crude product can be purified by chromatography or recrystallization.

In one example compound 21 can be dissolved in an organic solvent to which a solution of an acid in a solvent is added to form a salt of compound 21, which can be isolated by procedures known in the art. Examples of solvents include, but are not limited to acetonitrile, acetone, dichloromethane, chloroform, N,N-dimethylformamide, dimethyl sulfoxide, ethyl acetate, dichloroethane, water, benzene, toluene, xylene, methanol, ethanol, isopropanol and mixtures thereof. Examples of acids include hydrochloric acid, hydrobromic acid, methanesulfonic acid, 4-methylbenzensulfonic acid, sulfuric acid, phosphoric acid, citric acid, oxalic acid and the like. Compound 21 is then converted to remifentanil as described below.

The following table shows the different reagents that have been used for this reaction step.

| Solvent | Acylating agent | Base | Crystallization | Yield [%] |
|---|---|---|---|---|
| Acetonitrile | Propionyl chloride | TEA | IPA | 45 |
| Toluene | Propionyl chloride | TEA | IPA | 59 |
| chloroform | Propionyl chloride | TEA | IPA | 78 |
| Dichloromethane | Propionic anhydride | TEA | IPA | 65 |
| Dichloromethane | Propionyl chloride | Pyridine | IPA | 62 |
| DMF | Propionyl chloride | TEA | IPA | 58 |
| Dichloromethane | Propionyl chloride | TEA | IPA | 94 |
| Dichloromethane | Propionyl chloride | TEA | MEK/IPA | 89 |
| Dichloromethane | Propionyl chloride | TEA | EtOH | 81 |
| Dichloromethane | Propionyl chloride | TEA | acetone | 84 |

4. Use of Compound 20 in the Preparation of Compound 12

In another embodiment of the invention the new compound 20 is converted in one step to the known compound 12:

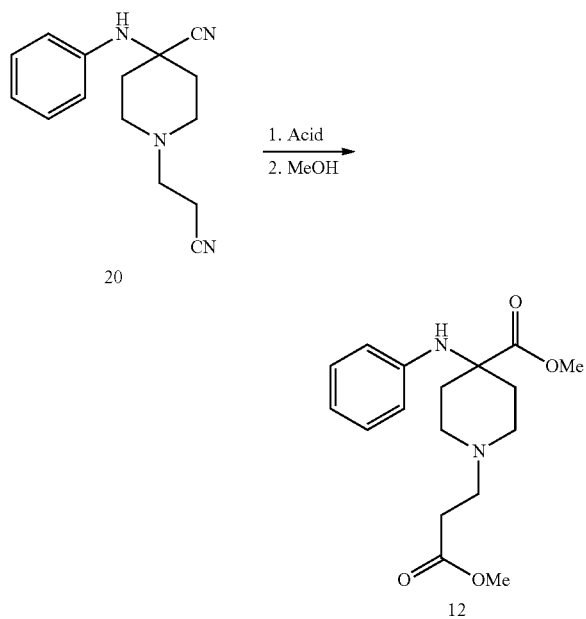

The synthesis of compound 12 is a one pot reaction taking place in a single reaction mixture wherein no intermediate amide product is isolated. The reaction may be conducted as described for example in WO2007061555. In a first reaction, compound 20 is hydrolyzed with an acid and water to form an intermediate amide in situ. The reaction mixture can optionally comprise a solvent.

In one embodiment, the reaction mixture comprises about 3 molar equivalents to about 10 molar equivalents of the acid to 1 molar equivalent of compound 20. In another embodiment, the reaction mixture comprises about 3 molar equivalents to about 5 molar equivalents of the acid to 1 molar equivalents of compound 20 In one embodiment, the reaction mixture temperature is from about −10° C. to about 40° C. In another example, the reaction mixture temperature is from about 15° C. to about 35° C. In still another example, the reaction mixture temperature is from about 10° C. to about 30° C.

The reaction mixture is permitted to react up to a couple of days. In one example, the reaction is carried out up to about 24 hours. In another example, the reaction time is from about 2 hours to 8 hours The acid source can be selected from organic or inorganic acids to adjust the pH of the reaction mixture below about 7. In one embodiment, the acid is selected from acetic acid, hydrochloric acid, sulfuric acid, methansulfonic acid, phosphoric acid, oxalic acid, and the like. In one example, the acid concentration is between 10% and about 99%, preferably between 70% and about 99%, with the balance comprising water. In still another example, the acid is selected from sulfuric acid or methansulfonic acid.

In one embodiment, the reaction mixture contains a solvent selected from the organic solvents described above for Scheme 2. In one example, the solvent comprises between about 10% to about 99% acid.

If the reaction takes place under anhydrous conditions, excess amount of alcohol is used as a solvent in the reaction mixture. In one embodiment, the alcohol is an aliphatic alcohol having 1 to 3 carbons.

In a second step an alcohol is added to the reaction mixture, wherein. The intermediate amide is esterified to form compound 12.

In another embodiment, the nitrile compound may be added to a mixture of alcohol and acid in one step to form the corresponding ester 12 via a Pinner-salt.

In one embodiment, about 10 parts to about 50 parts of alcohol are added to the reaction mixture. In one example, about 10 parts to about 20 parts of alcohol are added to the reaction mixture.

In one embodiment, the reaction mixture temperature is from about −10° C. to about 75° C. In another example, the reaction mixture temperature is from about 40° C. to about 65° C. The reaction mixture is permitted to react for about 24 hours to about 150 hours. In another example, the reaction time is from about 60 hours to about 100 hours.

Compound 12 can be isolated by utilizing isolation procedures known in the art such as those described for the above schemes.

5. Use of New Compound 21 in the Preparation of Remifentanil

In the final step 1-(2-cyanoethyl)-4-[phenyl(propanoyl) amino]piperidine-4-carbonitrile (21) reacts with methanol in acidic conditions to give Methyl 1-(3-methoxy-3-oxopropyl)-4-[phenyl(propanoyl)amino] piperidine-4-carboxylate hydrochloride (Remifentanil hydrochloride, 1)

Scheme 10 Preparation of Remifentanil hydrochloride from compound 21

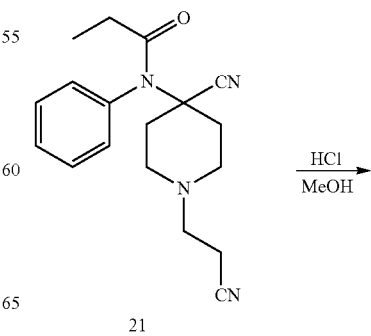

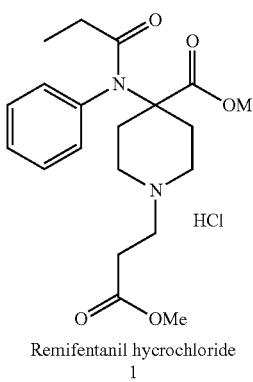

Remifentanil hydrochloride
1

In one embodiment the reaction mixture comprises of about 5 molar equivalent to about 20 molar equivalent of hydrochloric acid to 1 molar equivalent of 1-(2-cyanoethyl)-4-[phenyl(propanoyl)amino]piperidine-4-carbonitrile 21 In one embodiment methanol is used as solvents and acetone, acetonitrile, methanol, ethanol, isopropanol, methyl ethyl ketone are used as solvents for crystallization. The compound 21 to solvent ration on wt. basis is about 1:2 to 1:10.

The temperature of the reaction mixture during reaction ranges from about 0° C. to about 50° C. The reaction mixture is allowed to react up to several days. In one example the reaction time is from about 10 hours to 30 hours.

Compound 1 can be isolated by using isolation procedures known in the art.

The following table shows the different reagents that have been used for this reaction step.

| HCl in Methanol | Temperature | Crystallization | Yield [%] |
|---|---|---|---|
| 8:1 | r.t | IPA | 54 |
| 10:1 | r.t. | IPA | 63 |
| 8:1 | 40° C. | 1. IPA<br>2. MEK:IPA | 47 |
| 10:1 | 40° C. | Acetone:MeOH | 54 |
| 8:1 | reflux | MEK:IPA (2:3) | 64 |
| 10:1 | 40° C. | EtOH | 51 |
| 10:1 | 40° C. | MeOH | 72 |

6. Preparation of New Compound 20

Compound 20 may be synthesized in one step from the commercially available 3-(4-Oxopiperidin-1-yl)propanenitrile 19 with phenylamine in the presence of a cyanide compound and an acid.

Scheme 8 below illustrates the process wherein 3-(4-oxo-piperidine-1-yl)propanenitrile reacts with aniline and a cyanide containing reagent in the presence of an acid to give 1-(2-cyanoethyl)-4-(phenylamino)piperidine-4-carbonitrile 20.

Scheme 8 Preparation of intermediate 20

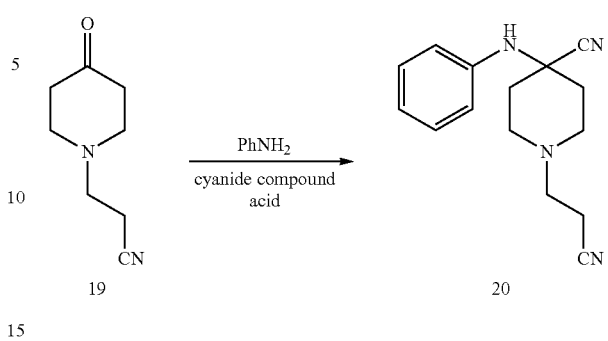

In one embodiment the reaction mixture comprises of about 1 molar equivalent to about 3 molar equivalents of aniline, about 1 molar equivalent to about 3 molar equivalents of cyanide compound and about 2 molar equivalents to 5 molar equivalents of acid to 1 molar equivalent of 19. Preferably, the reaction mixture is charged with about 1 to 1.5 equivalent of aniline, about 1 to 1.5 equivalent of cyanide compound and about 3-4 equivalent of acid to 1 equivalent of 3-(4-oxo-piperidine-1-yl)propanenitrile. The compound 19 to solvent ration on wt. basis is about 1:5 to 1:20.

The temperature of the reaction mixture during reaction ranges from about 0° C. to about 80° C. Preferably, the reaction temperature ranges from about 20° C. to about 60° C. The reaction mixture is allowed to react up to several days. In one example the reaction time is from about 2 hours to 5 hours.

The non-limiting examples of cyanide compounds are sodium cyanide, potassium cyanide, trimethylsilyl cyanide, hydrogen cyanide and the like.

Due to economic reasons, sodium cyanide is preferred.

The acid may include any organic and inorganic acid to adjust the pH below 7. Non-limiting examples of acids include acetic acid, hydrochloric acid, sulfuric acid, phosphoric acid, oxalic acid and the like. In one embodiment acetic acid is utilized to adjust the pH below 7.

Examples of solvents used in the reaction mixture include, but are not limited to acetonitrile, dichloromethane, chloroform, N,N-dimethylformamide, dimethylsulfoxide, ethyl acetate, dichloroethane, water, benzene, toluene xylene, methanol, ethanol, isopropanol and mixtures thereof.

Compound 20 can be isolated through solvent extraction or precipitation from the reaction mixture. Compound 20 can be further purified by using purification procedure known in the art. In one example compound 20 can be dissolved in an organic solvent to which a solution of an acid in a solvent is added to form a salt of compound 20, which can be isolated by procedures known in the art. Examples of solvents include, but are not limited to acetonitrile, acetone, dichloromethane, chloroform, N,N-dimethylformamide, dimethyl sulfoxide, ethyl acetate, dichloroethane, water, benzene, toluene, xylene, methanol, ethanol, isopropanol and mixtures thereof. Examples of acids include hydrochloric acid, hydrobromic acid, methanesulfonic acid, 4-methylbenzensulfonic acid, sulfuric acid, phosphoric acid, citric acid, oxalic acid and the like.

The following table shows the different reagents that have been used for this reaction step.

| Solvent | Cyanide compound | Acid | Yield % |
|---|---|---|---|
| MeOH | NaCN | AcOH | 79 |
| DCM | NaCN | AcOH | 65 |
| MeTHF | NaCN | AcOH | 65 |
| toluen | NaCN | AcOH | 53 |
| ACN | NaCN | AcOH | 82 |
| MeOH/$H_2O$ | NaCN | AcOH | 50 |
| $H_2O$ | NaCN | AcOH | 78 |
| $H_2O$ | KCN | AcOH | 62 |
| $H_2O$ | NaCN | HCl | 51 |
| $H_2O$ | NaCN | $H_2SO_4$ | 45 |

7. Preparation of Compound 19

Scheme 7 below illustrates the reaction wherein 4-piperidone monohydrate hydrochloride reacts with propionitrile derivative 18 to give 3-(4-oxo-piperidine-1-yl)propanenitrile Scheme 7 Preparation of intermediate 19 from 4-piperidone

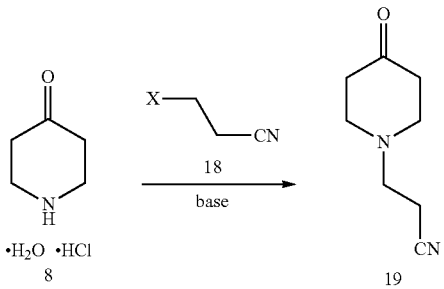

X: Cl, Br, I, OMs, OTs

In one embodiment compound 8 is mixed in a reaction mixture with propionitrile derivative 18 with a leaving group in position 3 in the presence of a solvent and a base to form intermediate 19. The reaction mixture comprises of about 1 molar equivalent to about 6 molar equivalents of 18 and about 1 molar equivalent to about 6 molar equivalent of base to 1 molar equivalent of 8. Preferably, the reaction mixture is charged with about 2 to 3 equivalent of 18 and about 2 to 4 equivalent of base to 1 equivalent of 4-piperidone monohydrate hydrochloride. The compound 8 to solvent ratio on wt. basis is about 1:3 to 1:20.

The temperature of the reaction mixture during reaction ranges from about 0° C. to about 80° C. The reaction mixture is allowed to react from about 6 h to about 48 h. In one example the reaction time is from about 18 hours to 24 hours.

Examples of propionitrile derivative 18 include 3-chloropropionitrile, 3-bromopropionitrile, 3-iodopropionitrile, 2-cyanoethyl methanesulfonate, 2-cyanoethyl 4-methylbenzenesulfonate.

Examples of the base include sodium hydroxide, potassium hydroxide, sodium carbonate, potassium carbonate, metal alkoxides, metal amides, metal hydrides and amines.

Examples of solvents used in the reaction mixture include, but are not limited to acetonitrile, acetone, methyl ethyl ketone, dichloromethane, chloroform, N,N-dimethylacetamide, N,N-dimethylformamide, dimethyl sulfoxide, ethyl acetate, dichloroethane, benzene, toluene, xylene, tetrahydrofuran, 2-methyl tetrahydrofuran and mixture thereof.

In one embodiment compound 19 can be isolated through solvent extraction and isolation procedure known in the art. Such isolation can include evaporation of solvent to recover the crude oily product.

In some examples compound 19 can be further purified by distillation or chromatography. In one example compound 19 can be dissolved in an organic solvent to which a solution of an acid in a solvent is added to form a salt of compound 19, which can be isolated by procedures known in the art. Examples of solvents include, but are not limited to acetonitrile, acetone, dichloromethane, chloroform, N,N-dimethylformamide, dimethyl sulfoxide, ethyl acetate, dichloroethane, water, benzene, toluene, xylene, methanol, ethanol, isopropanol and mixtures thereof. Examples of acids include hydrochloric acid, hydrobromic acid, sulfuric acid, phosphoric acid, citric acid, oxalic acid and the like.

The following table shows the different reagents that have been used for this reaction step.

| Solvent | Base | Alkylating agent | Yield [%] |
|---|---|---|---|
| DCM | $K_2CO_3$ | 3-chloropropionitrile | 75 |
| acetone | TEA | 3-bromopropionitrile | 76 |
| MEK | NaOH | 3-bromopropionitrile | 88 |
| MEK | $K_2CO_3$ | 3-chloropropionitrile | 85 |
| Acetone | $K_2CO_3$ | 3-bromopropionitrile | 69 |
| MeOH | $K_2CO_3$ | 2-cyanoethyl methanesulfonate | 68 |

8. Use of the New Compounds in the Synthesis of Remifentanil

Following the above mentioned a new method for the preparation of Remifentanil hydrochloride is described in the present invention. We have found that both methyl ester groups present in Remifentanil hydrochloride can be obtained from nitrile functions in the final step. The synthesis starts form 4-piperidone.$H_2O$.HCl and the target API is obtained after 4 reaction steps (Scheme 6).

Scheme 6 Preparation of Remifentanil hydrochloride described in the present invention

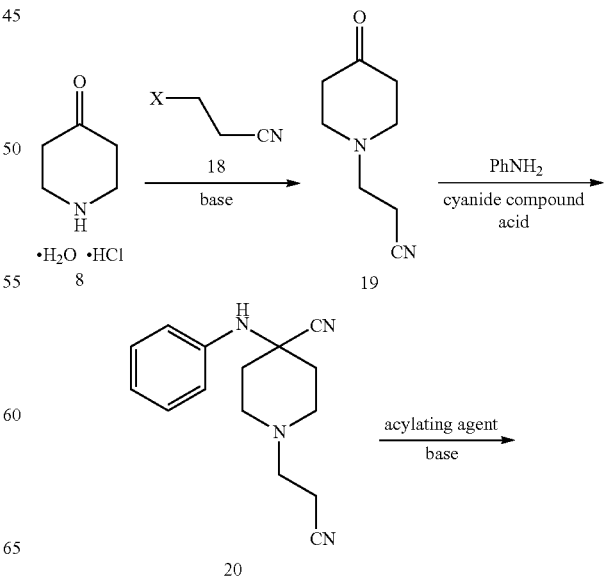

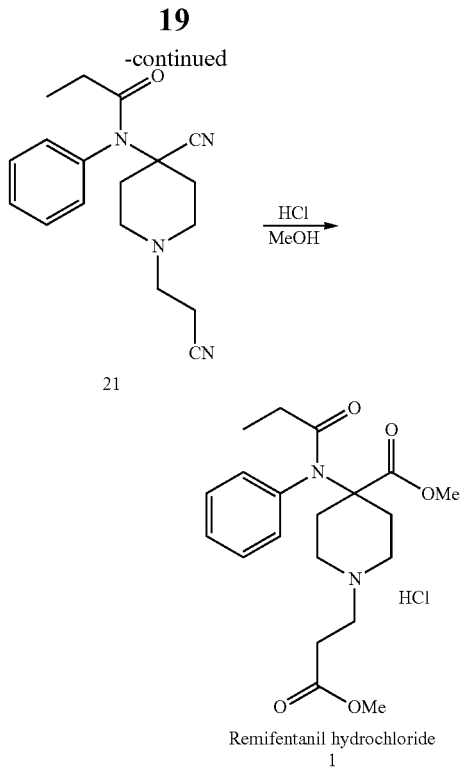

Remifentanil hydrochloride
1

EXAMPLES

The following examples are provided in order to more fully illustrate the present invention.

Example 1

Synthesis of 3-(4-oxopiperidin-1-yl)propanenitrile 5.10 mL (2 eq.) of 3-chloropropionitrile, 5.0 g of 4-piperidone monohydrate hydrochloride and 13.5 g (3 eq.) of K2CO3 were suspended in 40 mL of methyl ethyl ketone. The mixture was heated to 80° C. for 18 h. The solids were filtered off and the filtrate was concentrated under vacuum. Then it was dissolved in 30 mL of distilled water and extracted with ethyl acetate. The organic phase was dried over Na2SO4 and concentrated under vacuum: 4.21 g of 3-(4-oxopiperidin-1-yl)propanenitrile as a yellow liquid was obtained.

Example 2

Synthesis of 1-(2-cyanoethyl)-4-(phenylamino)piperidine-4-carbonitrile 1.69 g (1.05 eq.) of NaCN dissolved in 4.5 mL of distilled water was added dropwise (RT, ~30 min.) to a stirred solution of 5 g of 3-(4-oxopiperidin-1-yl)propanenitrile, 4.8 mL (1.6 eq.) of aniline and 4.9 mL (2.6 eq.) of acetic acid in 25 mL of methanol. The solution was heated to 60° C. for ca. 20 h. and then cooled down to 0° C. NaOH solution (33% w/v) was added dropwise while white precipitate was being formed (ca. 7 mL). Distilled water was added (10 mL) and the suspension was stirred at 0° C. for 6 h. The precipitate was filtered off, washed with H2O:MeOH (1:1) mixture and left to dry. Yield: 6.5 g (78%) of off-white powder.

Example 3

Synthesis of N-(4-cyano-1-(2-cyanoethyl)piperidin-4-yl)-N-phenylpropionamide 12.4 mL (3 eq.) of propionyl chloride was added dropwise to a cooled and stirred solution of 12 g of 1-(2-cyanoethyl)-4-(phenylamino) piperidine-4-carbonitrile in 120 mL of dichloromethane. Shortly, white precipitate formed. The mixture was refluxed overnight for ca. 20 h. and then allowed to reach RT. 6.5 mL (1 eq.) of triethylamine was added dropwise. The mixture turned transparent and gradually opaque again. After stirring at RT overnight (20 h.), 120 mL of distilled water was added. The separated organic phase was washed with 120 mL of sat. Na2CO3 solution, 120 mL of brine, dried over Na2SO4 and concentrated under vacuum: 8.2 g of crude light-brown matter was obtained. The crude product was crystallized from 40 mL of isopropanol. The precipitate was filtered off, washed with cold isopropanol and left to dry. Yield: 7.25 g (49%) of white powder.

Synthesis of Remifentanil HCl

Example 4

30 mL (15 eq.) of 35% HCl solution in methanol was added to 5 g of N-(4-cyano-1-(2-cyanoethyl)piperidin-4-yl)-N-phenylpropionamide and the mixture was stirred at room temperature. After 20 h., 5 mL of methanol was added and the suspension was stirred for additional 5 h. at room temperature. It was then filtered, the precipitate was washed with 5 mL of cold isopropanol and left to dry. The crude product contains an inorganic residue (NH4Cl) which can be filtered off during crystallization. 5.3 g of the crude product was suspended in 75 mL of isopropanol (13-15 mL/g) and refluxed for 15 min. While hot, the inorganic solid was filtered off and washed with 20 mL of hot isopropanol. The filtrate was refluxed again for 5 min., allowed to reach RT and cooling to 5° C. for 2 h. The crystal was filtered off, washed with isopropanol and left to dry. Yield: 2.18 g of white powdery crystals.

Example 5

30 mL (15 eq.) of 35% HCl solution in methanol was added to 5 g of N-(4-cyano-1-(2-cyanoethyl)piperidin-4-yl)-N-phenylpropionamide and the mixture was stirred at room temperature. After 20 h., 5 mL of methanol was added and the suspension was stirred for additional 5 h. at room temperature. It was then filtered, the precipitate was washed with 5 mL of cold isopropanol. The crude product was slowly added to 80 mL of stirred sat. Na2CO3 solution. The product was extracted with 2×40 mL of ethyl acetate. The organic phases were combined, dried over Na2SO4 and concentrated under reduced pressure. The obtained remifentanil base was dissolved in 15 mL of methanol, cooled to 5° C., and slowly added gaseous HCl (1.5 eq.). The precipitated hydrochloride salt was filtered off. Yield: 4.5 g of white powdery crystals.

What is claimed is:

1. A compound of formula 20 or a salt thereof:

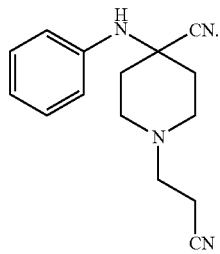

20

2. A method for synthesizing Remifentanil (1) or a salt thereof, the method selected from the group consisting of Method A and Method B, wherein Method A comprises reacting the compound of claim 1 or a salt thereof with an acylating agent, optionally in the presence of an acid scavenger, to produce a compound of formula (21), and reacting the compound of formula (21) with methanol under acidic conditions, and Method B comprises hydrolyzing the compound of claim 1 or a salt thereof with an acid, esterifying the hydrolyzed product with an alcohol to produce a compound of formula (12), and reacting the compound of formula (12) with an acylating agent, whereby Remifentanil (1) or a salt thereof is synthesized

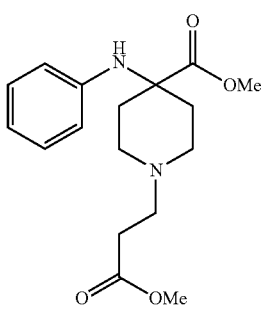

12

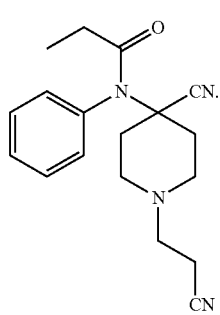

21

3. The method of claim 2, wherein the compound of formula (20) is first converted to a compound of formula (21)

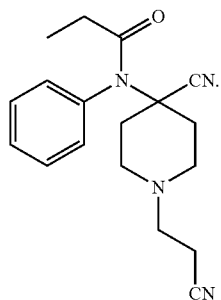

21

4. The method of claim 3, wherein the acylating agent is propionic anhydride or propionyl chloride.

5. The method of claim 4, wherein the acid scavenger is selected from the group consisting of triethylamine, morpholine, piperidine, and pyridine.

6. A method for preparing a compound of claim 1, the method comprising reacting a compound of formula (19) with phenylamine in the presence of a cyanide compound to produce a compound of formula (20).

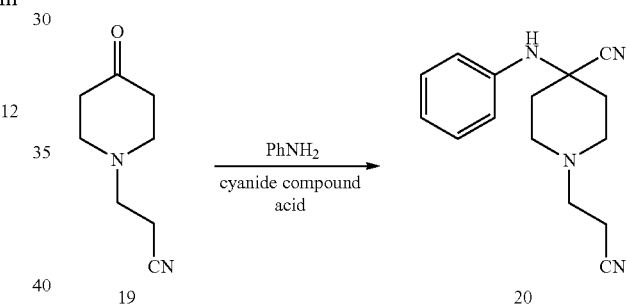

7. The method of claim 6, wherein the cyanide compound is sodium cyanide.

8. The method of claim 6, further comprising preparing the compound of formula (19) by alkylating 4-piperidone monohydrate hydrochloride with an appropriate alkylating agent in the presence of a basic catalyst, whereby a compound of formula (19) is prepared.

9. The method of claim 8, wherein the appropriate alkylating agent is selected from the group consisting of 3-chloropropionitrile, 3-bromopropionitrile, 3-iodopropionitrile, 2-cyanoethyl methanesulfonate, and 2-cyanoethyl 4-methyl benzenesulfonate.

10. The method of claim 9, wherein the basic catalyst is selected from the group consisting of sodium or potassium carbonate, sodium hydrogen carbonate, sodium or potassium hydroxide, sodium amide, potassium terc-butoxide, and sodium ethoxide.

11. The method of claim 8, wherein the alkylating is performed in the presence of a solvent, optionally wherein the solvent is selected from the group consisting of acetone, methyl ethyl ketone, isopropanol, acetonitrile, N,N-dimethylacetamide, N,N-dimethylformamide, tetrahydrofuran, and 2-methyl tetrahydrofuran.

12. A method for synthesizing remifentanil hydrochloride, wherein the method is according to the following scheme:

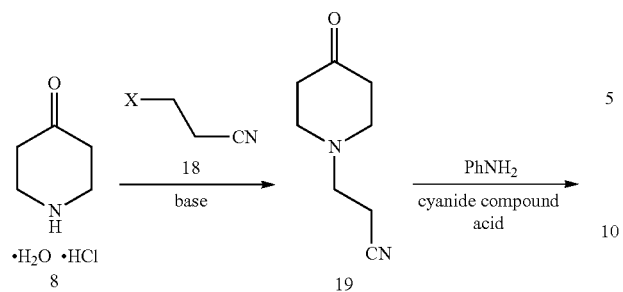
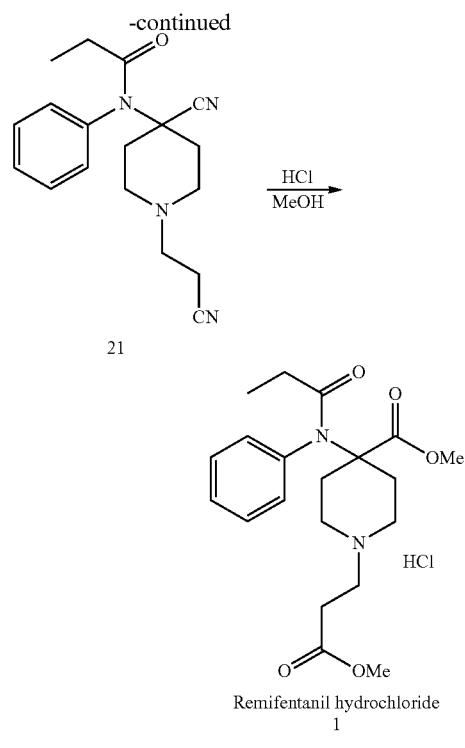

UNITED STATES PATENT AND TRADEMARK OFFICE
CERTIFICATE OF CORRECTION

| | | |
|---|---|---|
| PATENT NO. | : 10,844,014 B2 | |
| APPLICATION NO. | : 16/664464 | |
| DATED | : November 24, 2020 | |
| INVENTOR(S) | : Valachovic et al. | |

It is certified that error appears in the above-identified patent and that said Letters Patent is hereby corrected as shown below:

On the Title Page

Item (71)
Replace "Hameln Pharma Plus GmbH"
With --Hameln Pharma GmbH--.

Signed and Sealed this
Fourteenth Day of February, 2023

Katherine Kelly Vidal
*Director of the United States Patent and Trademark Office*